(12) United States Patent
Choi et al.

(10) Patent No.: US 8,314,927 B2
(45) Date of Patent: Nov. 20, 2012

(54) SYSTEMS AND METHODS FOR TESTING INTRAOCULAR LENSES

(75) Inventors: Steven Choi, Mountain View, CA (US); Terah Whiting Smiley, San Francisco, CA (US); Gregory Vinton Matthews, San Francisco, CA (US)

(73) Assignee: PowerVision, Inc., Belmont, CA (US)

( * ) Notice: Subject to any disclaimer, the term of this patent is extended or adjusted under 35 U.S.C. 154(b) by 175 days.

(21) Appl. No.: 12/178,454

(22) Filed: Jul. 23, 2008

(65) Prior Publication Data

US 2009/0027661 A1   Jan. 29, 2009

Related U.S. Application Data

(60) Provisional application No. 60/951,441, filed on Jul. 23, 2007.

(51) Int. Cl.
*G01M 11/02* (2006.01)
*G01M 11/08* (2006.01)
*A61F 2/16* (2006.01)

(52) U.S. Cl. .................... 356/124; 356/124.5; 623/6.13; 623/6.22; 623/6.37

(58) Field of Classification Search .......... 356/124–127; 351/210–213, 205, 206; 623/6.13, 6.22, 623/6.37, 6.34, 6.43, 6.44
See application file for complete search history.

(56) References Cited

U.S. PATENT DOCUMENTS

| | | | |
|---|---|---|---|
| 4,111,995 A | 9/1978 | Nelson | |
| 4,253,199 A | 3/1981 | Banko | |
| 4,254,509 A | 3/1981 | Tennant | |
| 4,304,895 A | 12/1981 | Loshaek | |
| 4,373,218 A | 2/1983 | Schachar | |
| 4,409,691 A | 10/1983 | Levy | |
| 4,423,809 A * | 1/1984 | Mazzocco | 206/5.1 |
| 4,435,856 A | 3/1984 | L'Esperance | |
| 4,466,705 A | 8/1984 | Michelson | |
| 4,490,860 A | 1/1985 | Rainin | |
| 4,494,254 A | 1/1985 | Lopez | |
| 4,512,040 A | 4/1985 | McClure | |
| 4,528,311 A | 7/1985 | Beard et al. | |
| 4,575,373 A | 3/1986 | Johnson | |
| 4,585,457 A | 4/1986 | Kalb | |
| 4,604,295 A | 8/1986 | Humphreys | |
| 4,615,701 A | 10/1986 | Woods | |
| 4,620,954 A | 11/1986 | Singer et al. | |
| 4,685,921 A | 8/1987 | Peyman | |
| 4,685,922 A | 8/1987 | Peyman | |
| 4,693,717 A | 9/1987 | Michelson | |

(Continued)

FOREIGN PATENT DOCUMENTS

EP     0898972 A2     3/1999

(Continued)

OTHER PUBLICATIONS

Smiley et al.; U.S. Appl. No. 12/178,565 entitled "Lens delivery system," filed Jul. 23, 2008.

(Continued)

*Primary Examiner* — Sang Nguyen

(74) *Attorney, Agent, or Firm* — Shay Glenn LLP

(57) ABSTRACT

Systems and their methods of use for testing intraocular lenses outside of the lens capsule. In some embodiments the systems measure an accommodative response based on a force applied to the intraocular lens.

21 Claims, 9 Drawing Sheets

U.S. PATENT DOCUMENTS

| | | | |
|---|---|---|---|
| 4,720,286 A | 1/1988 | Bailey et al. | |
| 4,731,078 A | 3/1988 | Stoy et al. | |
| 4,731,079 A | 3/1988 | Stoy | |
| 4,731,080 A | 3/1988 | Galin | |
| 4,784,485 A * | 11/1988 | Ho | 356/124 |
| 4,787,903 A | 11/1988 | Grendahl | |
| 4,790,847 A | 12/1988 | Woods | |
| 4,813,956 A | 3/1989 | Gupta | |
| 4,816,031 A | 3/1989 | Pfoff | |
| 4,836,201 A | 6/1989 | Patton et al. | |
| 4,836,202 A * | 6/1989 | Krasner | 606/107 |
| 4,842,601 A | 6/1989 | Smith | |
| 4,848,343 A | 7/1989 | Wallsten et al. | |
| 4,888,012 A | 12/1989 | Horn et al. | |
| 4,892,543 A | 1/1990 | Turely | |
| 4,902,293 A | 2/1990 | Feaster | |
| 4,919,151 A | 4/1990 | Grubbs et al. | |
| 4,932,966 A | 6/1990 | Christie et al. | |
| 4,946,469 A | 8/1990 | Sarafarazi | |
| 4,950,289 A | 8/1990 | Krasner | |
| 4,963,148 A | 10/1990 | Sulc et al. | |
| 4,994,082 A * | 2/1991 | Richards et al. | 623/6.32 |
| 4,995,879 A | 2/1991 | Dougherty | |
| 4,995,880 A | 2/1991 | Galib | |
| 5,015,254 A | 5/1991 | Greite | |
| 5,035,710 A | 7/1991 | Nakada et al. | |
| 5,047,051 A | 9/1991 | Cumming | |
| 5,061,914 A | 10/1991 | Busch et al. | |
| 5,066,301 A | 11/1991 | Wiley | |
| 5,078,740 A * | 1/1992 | Walman | 623/6.49 |
| 5,145,884 A | 9/1992 | Yamamoto et al. | |
| 5,145,935 A | 9/1992 | Hayashi | |
| 5,152,789 A | 10/1992 | Willis | |
| 5,171,266 A | 12/1992 | Wiley et al. | |
| 5,201,763 A | 4/1993 | Brady et al. | |
| 5,213,579 A | 5/1993 | Yamada et al. | |
| 5,224,957 A | 7/1993 | Gasser et al. | |
| 5,235,003 A | 8/1993 | Ward et al. | |
| 5,251,993 A | 10/1993 | Sigourney | |
| 5,275,623 A | 1/1994 | Sarfarazi | |
| 5,275,624 A | 1/1994 | Hara et al. | |
| 5,288,293 A | 2/1994 | O'Donnell, Jr. | |
| 5,290,892 A | 3/1994 | Namdaran et al. | |
| 5,326,347 A | 7/1994 | Cumming | |
| 5,405,386 A | 4/1995 | Rheinish et al. | |
| 5,443,506 A * | 8/1995 | Garabet | 623/6.13 |
| 5,444,106 A | 8/1995 | Zhou et al. | |
| 5,476,514 A | 12/1995 | Cumming | |
| 5,489,302 A | 2/1996 | Skottun | |
| 5,496,366 A | 3/1996 | Cumming | |
| 5,506,300 A | 4/1996 | Ward et al. | |
| 5,512,609 A | 4/1996 | Yang | |
| 5,578,081 A | 11/1996 | McDonald | |
| 5,585,049 A * | 12/1996 | Grisoni et al. | 264/1.7 |
| 5,593,436 A | 1/1997 | Langerman | |
| 5,607,472 A | 3/1997 | Thompson | |
| 5,628,795 A | 5/1997 | Langerman | |
| 5,633,504 A * | 5/1997 | Collins et al. | 250/461.1 |
| 5,665,822 A | 9/1997 | Bitler et al. | |
| 5,674,282 A | 10/1997 | Cumming | |
| 5,697,973 A | 12/1997 | Peyman et al. | |
| 5,702,441 A | 12/1997 | Zhou | |
| 5,772,666 A * | 6/1998 | Feingold et al. | 606/107 |
| 5,774,273 A | 6/1998 | Bornhorst | |
| 5,776,191 A | 7/1998 | Mazzocco | |
| 5,776,192 A | 7/1998 | McDonald | |
| 5,843,188 A | 12/1998 | McDonald | |
| 5,891,931 A | 4/1999 | Leboeuf et al. | |
| 5,928,282 A | 7/1999 | Nigam | |
| 5,964,802 A | 10/1999 | Anello et al. | |
| 5,984,962 A | 11/1999 | Anello et al. | |
| 6,013,101 A | 1/2000 | Israel | |
| 6,015,842 A | 1/2000 | Leboeuf et al. | |
| 6,102,539 A | 8/2000 | Tucker | |
| 6,117,171 A | 9/2000 | Skottun | |
| 6,124,980 A | 9/2000 | Cerbell | |
| 6,139,576 A | 10/2000 | Doyle et al. | |
| 6,160,084 A | 12/2000 | Langer et al. | |
| 6,176,878 B1 | 1/2001 | Gwon et al. | |
| 6,180,687 B1 | 1/2001 | Hammer et al. | |
| 6,188,526 B1 | 2/2001 | Sasaya et al. | |
| 6,190,410 B1 | 2/2001 | Lamielle et al. | |
| 6,195,807 B1 | 3/2001 | Chou | |
| 6,197,059 B1 | 3/2001 | Cumming | |
| 6,217,612 B1 | 4/2001 | Woods | |
| 6,225,367 B1 | 5/2001 | Chaouk et al. | |
| 6,229,641 B1 | 5/2001 | Kosaka | |
| 6,299,641 B1 | 10/2001 | Woods | |
| 6,302,911 B1 | 10/2001 | Hanna | |
| 6,322,589 B1 | 11/2001 | Cumming | |
| 6,342,073 B1 | 1/2002 | Cumming et al. | |
| 6,387,126 B1 | 5/2002 | Cumming | |
| 6,388,043 B1 | 5/2002 | Langer et al. | |
| 6,406,494 B1 | 6/2002 | Laguette et al. | |
| 6,413,262 B2 | 7/2002 | Saishin et al. | |
| 6,423,094 B1 | 7/2002 | Sarfarazi | |
| 6,443,985 B1 | 9/2002 | Woods | |
| 6,450,642 B1 | 9/2002 | Jethmalani et al. | |
| 6,464,725 B2 | 10/2002 | Skottun | |
| 6,471,708 B2 * | 10/2002 | Green | 606/107 |
| 6,488,708 B2 | 12/2002 | Sarfarazi | |
| 6,493,151 B2 | 12/2002 | Schachar | |
| 6,503,276 B2 * | 1/2003 | Lang et al. | 623/6.37 |
| 6,517,577 B1 * | 2/2003 | Callahan et al. | 623/6.49 |
| 6,524,340 B2 * | 2/2003 | Israel | 623/6.44 |
| 6,551,354 B1 * | 4/2003 | Ghazizadeh et al. | 623/6.43 |
| 6,552,860 B1 | 4/2003 | Alden | |
| 6,554,859 B1 | 4/2003 | Lang et al. | |
| 6,585,768 B2 * | 7/2003 | Hamano et al. | 623/6.37 |
| 6,589,550 B1 | 7/2003 | Hodd et al. | |
| 6,592,621 B1 | 7/2003 | Domino | |
| 6,599,317 B1 | 7/2003 | Weinschenk, III et al. | |
| 6,601,956 B1 * | 8/2003 | Jean et al. | 351/212 |
| 6,610,350 B2 | 8/2003 | Suzuki et al. | |
| 6,616,691 B1 | 9/2003 | Tran | |
| 6,616,692 B1 | 9/2003 | Glick et al. | |
| 6,638,304 B2 | 10/2003 | Azar | |
| 6,638,305 B2 | 10/2003 | Laguette | |
| 6,638,306 B2 | 10/2003 | Cumming | |
| 6,645,245 B1 | 11/2003 | Preussner | |
| 6,645,246 B1 | 11/2003 | Weinschenk, III et al. | |
| 6,656,223 B2 * | 12/2003 | Brady | 623/6.46 |
| 6,660,035 B1 | 12/2003 | Lang et al. | |
| 6,692,525 B2 | 2/2004 | Brady et al. | |
| 6,695,881 B2 | 2/2004 | Peng et al. | |
| 6,709,108 B2 | 3/2004 | Levine et al. | |
| 6,712,848 B1 | 3/2004 | Wolf et al. | |
| 6,730,123 B1 | 5/2004 | Klopotek | |
| 6,743,388 B2 | 6/2004 | Sridharan et al. | |
| 6,749,632 B2 | 6/2004 | Sandstedt et al. | |
| 6,749,634 B2 | 6/2004 | Hanna | |
| 6,786,934 B2 | 9/2004 | Zadno-Azizi et al. | |
| 6,818,158 B2 | 11/2004 | Pham et al. | |
| 6,827,738 B2 | 12/2004 | Willis et al. | |
| 6,836,374 B2 | 12/2004 | Esch et al. | |
| 6,860,601 B2 | 3/2005 | Shadduck | |
| 6,878,320 B1 | 4/2005 | Alderson et al. | |
| 6,884,261 B2 | 4/2005 | Zadno-Azizi et al. | |
| 6,884,263 B2 * | 4/2005 | Valyunin et al. | 623/6.37 |
| 6,899,732 B2 | 5/2005 | Zadno-Azizi et al. | |
| 6,899,850 B2 * | 5/2005 | Haywood et al. | 422/102 |
| 6,914,247 B2 * | 7/2005 | Duggan et al. | 250/341.8 |
| 6,926,736 B2 | 8/2005 | Peng et al. | |
| 6,935,743 B2 | 8/2005 | Shadduck | |
| 6,966,649 B2 | 11/2005 | Shadduck | |
| 6,969,403 B2 | 11/2005 | Peng et al. | |
| 7,060,094 B2 | 6/2006 | Shahinpoor et al. | |
| 7,068,439 B2 | 6/2006 | Esch | |
| 7,122,053 B2 | 10/2006 | Esch | |
| 7,144,423 B2 | 12/2006 | McDonald | |
| 7,217,288 B2 | 5/2007 | Esch et al. | |
| 7,241,312 B2 | 7/2007 | Lai et al. | |
| 7,247,689 B2 | 7/2007 | Makker et al. | |
| 7,264,351 B2 | 9/2007 | Shadduck | |
| 7,276,619 B2 | 10/2007 | Kunzler et al. | |
| 7,278,739 B2 | 10/2007 | Shadduck | |
| 7,311,194 B2 * | 12/2007 | Jin et al. | 206/5.1 |

| | | |
|---|---|---|
| 7,416,300 B2 | 8/2008 | Wei et al. |
| 7,416,562 B2 * | 8/2008 | Gross ............... 623/6.13 |
| 7,453,646 B2 | 11/2008 | Lo |
| 7,485,144 B2 * | 2/2009 | Esch ................ 623/6.13 |
| 7,494,505 B2 | 2/2009 | Kappelhof et al. |
| 7,591,849 B2 * | 9/2009 | Richardson ........... 623/6.47 |
| 7,675,686 B2 | 3/2010 | Lo et al. |
| 7,753,953 B1 | 7/2010 | Yee |
| 7,763,069 B2 | 7/2010 | Brady et al. |
| 7,794,498 B2 | 9/2010 | Pinchuk |
| 7,988,290 B2 | 8/2011 | Campbell et al. |
| 7,988,292 B2 | 8/2011 | Neal et al. |
| 2001/0001836 A1 | 5/2001 | Cumming |
| 2001/0016771 A1 | 8/2001 | Cumming |
| 2001/0039449 A1 | 11/2001 | Johnson et al. |
| 2002/0046783 A1 | 4/2002 | Johnson et al. |
| 2002/0055777 A1 | 5/2002 | Cumming et al. |
| 2002/0072795 A1 | 6/2002 | Green |
| 2002/0095212 A1 | 7/2002 | Boehm |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0133228 A1 | 9/2002 | Sarver |
| 2002/0161434 A1 | 10/2002 | Laguette et al. |
| 2002/0161435 A1 | 10/2002 | Portney |
| 2002/0177896 A1 | 11/2002 | Israel |
| 2002/0193876 A1 | 12/2002 | Lang et al. |
| 2003/0003295 A1 | 1/2003 | Dreher et al. |
| 2003/0004569 A1 | 1/2003 | Haefliger |
| 2003/0018384 A1 | 1/2003 | Valyunin et al. |
| 2003/0042176 A1 | 3/2003 | Alderson et al. |
| 2003/0050695 A1 | 3/2003 | Lin et al. |
| 2003/0050696 A1 | 3/2003 | Cumming |
| 2003/0060878 A1 | 3/2003 | Shadduck |
| 2003/0060881 A1 | 3/2003 | Glick et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0109925 A1 | 6/2003 | Ghazizadeh et al. |
| 2003/0109926 A1 | 6/2003 | Portney |
| 2003/0130732 A1 | 7/2003 | Sarfarazi |
| 2003/0135272 A1 | 7/2003 | Brady et al. |
| 2003/0149480 A1 | 8/2003 | Shadduck |
| 2003/0158599 A1 | 8/2003 | Brady et al. |
| 2003/0171808 A1 | 9/2003 | Phillips |
| 2003/0183960 A1 | 10/2003 | Buazza et al. |
| 2003/0187505 A1 | 10/2003 | Liao |
| 2003/0199977 A1 | 10/2003 | Cumming |
| 2003/0236376 A1 | 12/2003 | Kindt-Larsen et al. |
| 2004/0001180 A1 | 1/2004 | Epstein |
| 2004/0006386 A1 | 1/2004 | Valint et al. |
| 2004/0006387 A1 | 1/2004 | Kelman |
| 2004/0008419 A1 | 1/2004 | Schachar |
| 2004/0015236 A1 | 1/2004 | Sarfarazi |
| 2004/0039446 A1 | 2/2004 | McNicholas |
| 2004/0054408 A1 | 3/2004 | Glick et al. |
| 2004/0059343 A1 | 3/2004 | Shearer et al. |
| 2004/0082993 A1 | 4/2004 | Woods |
| 2004/0082994 A1 | 4/2004 | Woods et al. |
| 2004/0085511 A1 | 5/2004 | Uno et al. |
| 2004/0088050 A1 | 5/2004 | Norrby et al. |
| 2004/0111151 A1 | 6/2004 | Paul et al. |
| 2004/0111152 A1 | 6/2004 | Kelman |
| 2004/0111153 A1 | 6/2004 | Woods et al. |
| 2004/0127984 A1 | 7/2004 | Paul et al. |
| 2004/0162612 A1 | 8/2004 | Portney et al. |
| 2004/0181279 A1 | 9/2004 | Nun |
| 2004/0190153 A1 | 9/2004 | Esch |
| 2004/0230203 A1 | 11/2004 | Yaguchi |
| 2005/0021139 A1 | 1/2005 | Shadduck |
| 2005/0119740 A1 | 6/2005 | Esch et al. |
| 2005/0131535 A1 | 6/2005 | Woods |
| 2005/0149183 A1 | 7/2005 | Shadduck |
| 2005/0165410 A1 | 7/2005 | Zadno-Azizi et al. |
| 2005/0251253 A1 | 11/2005 | Gross |
| 2005/0264756 A1 | 12/2005 | Esch |
| 2006/0041307 A1 | 2/2006 | Esch et al. |
| 2006/0069433 A1 | 3/2006 | Nun |
| 2006/0100703 A1 | 5/2006 | Evans et al. |
| 2006/0116763 A1 | 6/2006 | Simpson |
| 2006/0134173 A1 | 6/2006 | Liu et al. |
| 2006/0184181 A1 | 8/2006 | Cole et al. |
| 2006/0200167 A1 | 9/2006 | Peterson et al. |
| 2006/0253196 A1 | 11/2006 | Woods |
| 2007/0004886 A1 | 1/2007 | Schorzman et al. |
| 2007/0005136 A1 | 1/2007 | Richardson |
| 2007/0010880 A1 | 1/2007 | Esch |
| 2007/0021831 A1 | 1/2007 | Clarke |
| 2007/0050023 A1 | 3/2007 | Bessiere et al. |
| 2007/0078515 A1 | 4/2007 | Brady |
| 2007/0088433 A1 | 4/2007 | Esch et al. |
| 2007/0100445 A1 | 5/2007 | Shadduck |
| 2007/0106377 A1 | 5/2007 | Smith et al. |
| 2007/0129801 A1 | 6/2007 | Cumming |
| 2007/0162112 A1 | 7/2007 | Burriesci et al. |
| 2007/0203578 A1 | 8/2007 | Scholl et al. |
| 2007/0213817 A1 | 9/2007 | Esch et al. |
| 2007/0244561 A1 | 10/2007 | Nun |
| 2007/0299487 A1 | 12/2007 | Shadduck |
| 2008/0004699 A1 | 1/2008 | Nun |
| 2008/0015689 A1 | 1/2008 | Esch et al. |
| 2008/0027537 A1 | 1/2008 | Gerlach et al. |
| 2008/0046074 A1 | 2/2008 | Smith et al. |
| 2008/0046075 A1 | 2/2008 | Esch et al. |
| 2008/0097460 A1 | 4/2008 | Boukhny et al. |
| 2008/0139769 A1 | 6/2008 | Iwamoto et al. |
| 2008/0179770 A1 | 7/2008 | Rooney et al. |
| 2008/0188930 A1 | 8/2008 | Mentak et al. |
| 2008/0269887 A1 | 10/2008 | Cumming |
| 2008/0269987 A1 | 10/2008 | Barron et al. |
| 2008/0300680 A1 | 12/2008 | Joshua |
| 2008/0306587 A1 | 12/2008 | Your |
| 2009/0076602 A1 | 3/2009 | Ho et al. |
| 2009/0228101 A1 | 9/2009 | Zadno-Azizi |
| 2009/0234449 A1 | 9/2009 | De Juan, Jr. et al. |
| 2009/0264998 A1 | 10/2009 | Mentak et al. |
| 2009/0281620 A1 | 11/2009 | Sacharoff et al. |
| 2009/0292293 A1 | 11/2009 | Bogaert et al. |
| 2009/0312836 A1 | 12/2009 | Pinchuk et al. |
| 2010/0039709 A1 | 2/2010 | Lo |
| 2010/0063588 A1 | 3/2010 | Park |
| 2010/0228344 A1 | 9/2010 | Shadduck |
| 2010/0228346 A1 | 9/2010 | Esch |
| 2010/0324671 A1 | 12/2010 | Shadduck |
| 2010/0324672 A1 | 12/2010 | Esch et al. |
| 2011/0118834 A1 | 5/2011 | Lo et al. |
| 2011/0153015 A1 | 6/2011 | Simonov et al. |
| 2011/0208301 A1 | 8/2011 | Anvar et al. |
| 2012/0078364 A1 | 3/2012 | Stenger |

FOREIGN PATENT DOCUMENTS

| | | |
|---|---|---|
| FR | 2784575 | 4/2000 |
| JP | 07-044938 | 5/1995 |
| JP | 9294754 | 11/1997 |
| JP | 10-206609 | 8/1998 |
| JP | 11276509 | 10/1999 |
| RU | 1810052 | 4/1993 |
| WO | WO 97/06751 A | 2/1997 |
| WO | WO 00/41650 A1 | 7/2000 |
| WO | WO 00/64655 A1 | 11/2000 |
| WO | WO 01/60286 A1 | 8/2001 |
| WO | WO 01/89435 A1 | 11/2001 |
| WO | WO 01/97742 A2 | 12/2001 |
| WO | WO 02/051338 | 7/2002 |
| WO | WO 2004/010895 A2 | 2/2004 |
| WO | WO 2004/046768 A2 | 6/2004 |
| WO | WO 2004/072689 A2 | 8/2004 |
| WO | WO 2005/084588 A1 | 9/2005 |
| WO | WO 2006/004707 A2 | 1/2006 |
| WO | WO2006011937 A2 | 2/2006 |
| WO | WO 2006/047383 A2 | 5/2006 |
| WO | WO 2006/088440 A1 | 8/2006 |
| WO | WO 2007/005529 A2 | 1/2007 |

| WO | WO 2007/030095 A1 | 3/2007 |
| WO | WO 2007/061688 A2 | 5/2007 |
| WO | WO 2007/128423 A1 | 11/2007 |
| WO | WO2007/138564 A1 | 12/2007 |
| WO | WO 2009/100322 A2 | 8/2009 |
| WO | WO 2009/154455 A1 | 12/2009 |

OTHER PUBLICATIONS

Lendlein et al., "Biodegradable, elastic shape-memory polymers for potential biomedical applications", Science; vol. 296; pp. 1673-1676; May 31, 2002.

Lendlein et al., "Shape-memory polymers," Angew. Chem. Int. Ed.; vol. 41; pp. 2034-2057; 2002.

Shadduck, John H.; U.S. Appl. No. 12/347,816 entitled "Intraocular lenses and business methods," filed Dec. 31, 2008.

Gruber et al.; Exhaustive soxhlet extraction for the complete removal of residual compounds . . . ; Journal of Biomedical Materials Research; vol. 53; No. 5; pp. 445-448; Mar. 2000.

Shadduck, John H.; U.S. Appl. No. 12/694,184 entitled "Intraocular Lenses and Business Methods," filed Jan. 26, 2010.

Argento et al.; U.S. App. No. 12/685,531 entitled "Intraocular Lenses and Methods of Accounting for Capsule Size Variability and Post-Implant Changes in the Eye," filed Jan. 11, 2010.

Baughman et al., "Negative poisson's ratios for extreme states fo matter," Science, vol. 288, pp. 1028-2022, Jun. 16, 2000.

Baughman, "Avoiding the shrink," Nature, vol. 425, pp. 667, Oct. 16, 2003.

Gordon, "Applications of shape memory polyurethanes," Proceedings of the First Intl Conf. on Shape Memory and Superelastic Tech., Asilomar Conference Center, Pacific Grove, CA, USA, pp. 115-119, 1994.

Jeon et al., "Shape memory and nonstructure in poly(norbomyl-POSS) copolymers," Polymer International, vol. 49, pp. 453-457, 2000.

Kim et al., "Polyurethanes having shape memory effects," Polymer, vol. 37, No. 26, pp. 5781-5793, 1996.

Lakes et al., "Dramatically stiffer elastic composite materials due to negative stiffness phase?," Journal of the Mechanics and Physics of Solids, vol. 50, pp. 979-1009, 2002.

Lakes et al., "Extreme damping in composite materials with negative-stiffness inclusions," Nature, vol. 410, pp. 565-567, Mar. 29, 2001.

Lakes, "A broader view of membranes," Nature, vol. 414, pp. 503-504, Nov. 29, 2001.

Lakes, "Extreme damping in compliant composites with a negative-stiffness phase," Philosophical Magazine Letters, vol. 81, No. 2, pp. 95-100, 2001.

Lakes, "Extreme damping in composite materials with a negative stiffness phase," Physical Review Letters, vol. 86, No. 13, pp. 2897-2899, Mar. 26, 2001.

Lakes, "Lateral deformations in extreme matter," Science, vol. 288, pp. 1976, Jun. 2000.

Lakes, "Negative poisson's ratio materials," Science, vol. 238, pp. 551, Oct. 23, 1987.

Lakes, "No contractile obligations," Nature, vol. 358, pp. 713-714, 1992.

Li et al., "Crystallinity and morphology of segmented polyurethanes with different soft-segment length," Journal of Applied Polymer Science, vol. 62, pp. 631-638, 1996.

Liu et al., "Thermomechanical characterization of a tailored series of shape memory polymers," Journal of Applied Medical Polymers, vol. 6, No. 2, 2002.

Mather et al., "Strain recovery in POSS hybrid thermoplastics," Polymer Preprints, vol. 41, No. 1, pp. 528-529, 2000.

Metcalfe et al., "Cold hibernated elastic memory foams for endovascular interventions," Biomaterials, vol. 24, pp. 491-497, 2003.

Lakes et al., "Microbuckling instability in elastomeric cellular sollids," J. Materials Science, vol. 28, pp. 4667-4672, 1993.

Takahashi et al., "Structure and properties of shape-memory polyurethane block copolymers," Journal of Applied Polymer Science, vol. 60, pp. 1061-1069, 1996.

Tobushi et al., "Thermomechanical properties of shape memory polymers of polyurethane series and their applications," Journal de Physique IV, Colloque C1, vol. 6, pp. 377-384, 1996.

Wang et al., "Deformation of extreme viscoelastic metals and composites," Materials Science and Engineering A, vol. 370, pp. 41-49, 2004.

Wang et al., "Extreme stiffness systems due to negative stiffness elements," American Journal of Physics, vol. 72, No. 1, pp. 40-50, Jan. 2004.

Wang et al., "Stable extremely-high-damping discrete viscoelastic systems due to native stiffness elements," Applied Physics Letters, vol. 84, No. 22, pp. 4451-4453, May 31, 2004.

Wyant et al; "Basic Wavefront Aberration Theory for Optical Metrology," Applied Optics and Optical Engineering, vol. XI, 1992:1-13.

Xu et al., "Basic negative poisson's ratio microstructures by soft lithography," Advanced Materials, vol. 11, No. 14, 1999, pp. 1186-1189, 1999.

Your, Jingjong; U.S. Appl. No. 12/034,942 entitled "Polymeric materials suitable for ophthalmic devices and methods of manufacture," filed Feb. 21, 2008.

Your, Jingjong; U.S. Appl. No. 12/177,720 entitled "Lens material and methods of curing with UV light," filed Jul. 22, 2008.

Smiley et al.; U.S. Appl. No. 12/177,857 entitled "Accommodating intraocular lenses and methods of use," filed Jul. 22, 2008.

Smiley et al.; U.S. Appl. No. 12/178,304 entitled "Post-implant accommodating lens modification," filed Jul. 23, 2008.

Hildebrand et al.; U.S. Appl. No. 12/872,314 entitled "Lens Capsule Size Estimation," filed Aug. 31, 2010.

Conlisk, A. T. et al; Mass Transfer and Flow in Electrically Charged Micro- and Nano-channels; Analytical Chemistry, vol. 74; iss. 9; pp. 2139-2150; 2002.

Dubbelman et al.; The Thickness of the Aging Human Lens Obtained from Corrected Scheimpflug Images; Optometry & Vison Science; vo. 78; iss. 6; pp. 411-416; Jun. 2001.

Gorder, P. F.; Electricity can pump medicine in implanted medical devices; Ohio State Research News; 3 pgs.; May 2, 2002 (printed from internet Aug. 19, 2010).

Tehrani et al.; Capsule measuring ring to predict capsular bag diameter and follow its course after foldable intraocular lens implantation; J Cataract Refract Surg.; vol. 29; No. 11; pp. 2127-2134; Nov. 2003.

Vass et al.; Prediction of pseudophakic capsular bag diameter based on biometric variables; J Cataract Refract Surg.; vol. 25; pp. 1376-1381; 1999.

Scholl et al.; U.S. Appl. No. 13/193,487 entitled "Accommodating Intraocular Lenses," filed Jul. 28, 2011.

Smiley et al.; U.S. Appl. No. 13/193,983 entitled "Accommodating Intraocular Lenses," filed Jul. 29, 2011.

Smiley et al.; U.S. Appl. No. 13/194,004 entitled "Accommodating Intraocular Lenses," filed Jul. 29, 2011.

Hildebrand et al.; U.S. Appl. No. 13/180,427 entitled "Intraocular lens delivery devices and methods of use," filed Jul. 11, 2011.

Shadduck, John H.; U.S. Appl. No. 13/300,245 entitled "Accommodating Intraocular Lenses and Methods of Use," filed Nov. 18, 2011.

* cited by examiner

SYSTEMS AND METHODS FOR TESTING INTRAOCULAR LENSES

CROSS-REFERENCE TO RELATED APPLICATIONS

This application claims the benefit of U.S. Provisional Application No. 60/951,441, filed Jul. 23, 2007, which is hereby incorporated by reference as if fully set forth herein.

BACKGROUND OF THE INVENTION

Cataracts are a major cause of blindness in the world and the most prevalent ocular disease. When the disability from cataracts affects or alters an individual's activities of daily living, surgical lens removal with intraocular lens ("IOL") implantation is the preferred method of treating the functional limitations.

A cataract is any opacity of a patient's lens, whether it is a localized opacity or a diffuse general loss of transparency. To be clinically significant, however, the cataract must cause a significant reduction in visual acuity or a functional impairment. A cataract occurs as a result of aging or secondary to hereditary factors, trauma, inflammation, metabolic or nutritional disorders, or radiation. Age related cataract conditions are the most common.

In treating a cataract, the surgeon removes the crystalline lens matrix from the lens capsule and replaces it with an IOL. The typical IOL provides a selected focal length that allows the patient to have fairly good distance vision. Since the lens can no longer accommodate, however, the patient typically needs glasses for reading.

More specifically, the imaging properties of the human eye are facilitated by several optical interfaces. A healthy youthful human eye has a total power of approximately 59 diopters, with the anterior surface of the cornea (e.g. the exterior surface, including the tear layer) providing about 48 diopters of power, while the posterior surface provides about −4 diopters. The crystalline lens, which is situated posterior of the pupil in a transparent elastic capsule, also referred to herein as "capsular sac," supported by the ciliary muscles via zonules, provides about 15 diopters of power, and also performs the critical function of focusing images upon the retina. This focusing ability, referred to as "accommodation," enables imaging of objects at various distances.

The power of the lens in a youthful eye can be adjusted from 15 diopters to about 29 diopters by adjusting the shape of the lens from a moderately convex shape to a highly convex shape. The mechanism generally accepted to cause this adjustment is that ciliary muscles supporting the capsule (and the lens contained therein) move between a relaxed state (corresponding to the moderately convex shape) and a contracted state (corresponding to the highly convex shape). Because the lens itself is composed of viscous, gelatinous transparent fibers, arranged in an "onion-like" layered structure, forces applied to the capsule by the ciliary muscles via the zonules cause the lens to change shape.

Isolated from the eye, the relaxed capsule and lens take on a more spherical shape. Within the eye, however, the capsule is connected around its circumference by approximately 70 tiny ligament fibers to the ciliary muscles, which in turn are attached to an inner surface of the eyeball. The ciliary muscles that support the lens and capsule therefore are believed to act in a sphincter-muscular mode. Accordingly, when the ciliary muscles are relaxed, the capsule and lens are pulled about its circumference to a larger diameter, thereby flattening the lens, whereas when the ciliary muscles are contracted the lens and capsule relax somewhat and assume a smaller diameter that approaches a more spherical shape.

As noted above, the youthful eye has approximately 14 diopters of accommodation. As a person ages, the lens hardens and becomes less elastic, so that by about age 45-50, accommodation is reduced to about 2 diopters. At a later age the lens may be considered to be non-accommodating, a condition known as "presbyopia". Because the imaging distance is fixed, presbyopia typically entails the need for bifocals to facilitate near and far vision.

Apart from age-related loss of accommodation ability, such loss is innate to the placement of IOLs for the treatment of cataracts. IOLs can be single element lenses made from a suitable polymer material, such as acrylics or silicones. After placement, accommodation is no longer possible, although this ability is typically already lost for persons receiving an IOL. There is significant need to provide for accommodation in IOL products so that IOL recipients will have accommodating ability. In addition, although efforts have been made with accommodating IOLs, there is a need for an accommodating IOL that can restore as much accommodation to the eye as possible.

What is needed is a device to test an accommodative intraocular lens to measure the intraocular lens's accommodative response to a force that is applied to it. It may also be desirable that the device be able to measure the intraocular lens's accommodative response to a simulated external actuation of the lens.

SUMMARY OF THE INVENTION

One aspect of the invention is a method of testing an accommodative response of an intraocular lens. The method includes applying a force to the intraocular lens when the intraocular lens is outside of a lens capsule and measuring an accommodative response of the intraocular lens based on the applied force.

In some embodiments wherein applying a force to the intraocular lens comprises applying a force to a peripheral portion of the intraocular lens.

In some embodiments applying a force to the intraocular lens comprises applying a compressive force to the intraocular lens. Applying a compressive force can comprises applying a radially compressive force to the intraocular lens.

In some embodiments applying a force to the intraocular lens comprises displacing a flowable media within the intraocular lens from a peripheral portion of the intraocular lens to an optic portion of the intraocular lens.

In some embodiments measuring an accommodating response of the intraocular lens comprises measuring the deflection of a surface of the intraocular lens.

In some embodiments measuring the deflection of a surface of the intraocular lens comprises measuring the deflection of an anterior surface of the intraocular lens.

In some embodiments measuring an accommodative response of the intraocular lens comprises optically measuring an accommodative response of the intraocular lens.

In some embodiments the method also includes measuring the force applied to the intraocular lens and relating it to the measured accommodative response.

In some embodiments measuring an accommodative response of the intraocular lens comprises measuring a change of configuration of the lens or a portion of the lens.

One aspect of the invention is a system for measuring an accommodative response of an intraocular lens outside of a lens capsule. The system comprises a force effector adapted to apply a force on an intraocular lens and an accommodative response measuring element adapted to measure an accommodative response of the intraocular lens based on the force applied by the force effectors.

In some embodiments the force effector is adapted to apply a radially compressive force on the intraocular lens.

In some embodiments the force effector is a first force effector and the system further comprises a second force effector, wherein the first force effector is disposed substantially opposite the second force effector around the periphery of the intraocular lens.

In some embodiments the force effector is a first force effector and the system further comprises a second force effector, wherein the first force effector is adapted to be actuated with a first compression actuator to apply a force to intraocular lens and the second force effector is adapted to be actuated with a second compression actuator to apply a second force to the intraocular lens.

In some embodiments the system further comprises a force measuring element adapted to measure the force applied to the intraocular lens. In some embodiments the force measuring element is a load cell.

In some embodiments the accommodative response measuring element is adapted to measure deflection of a surface of the intraocular lens. The accommodative response measuring element comprises can be a microscope adapted to sense a focus plane on a surface of the intraocular lens.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The invention relates generally to systems and devices for testing an intraocular lens ("IOL") and in some embodiments systems for testing accommodating IOLs. The devices are adapted to test the intraocular lens outside of the lens capsule. In some embodiments the IOL includes a flowable media (such as a fluid, gelatinous material, etc.) that is moved within the IOL, in response to ciliary muscle movement, to change the power of the IOL.

Figure 1:
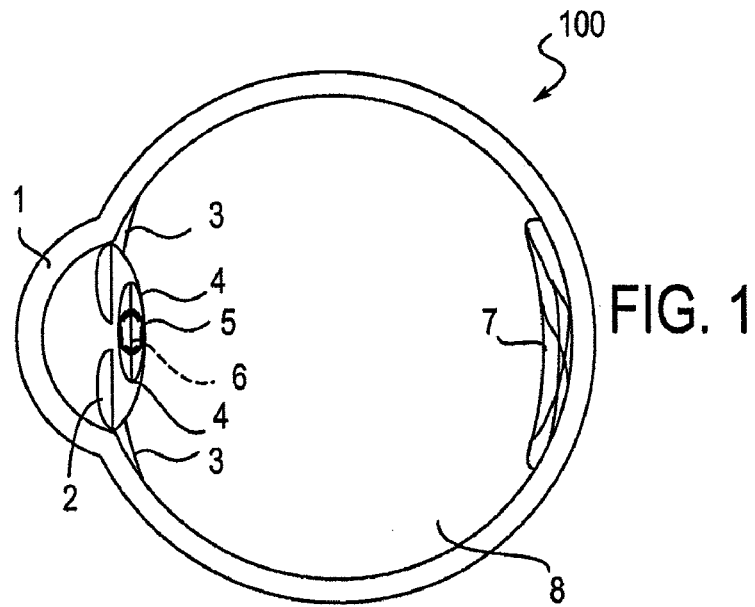
FIGS. 1, 2A, and 2B illustrate the structure and operation of a human eye.
Figure 2A:
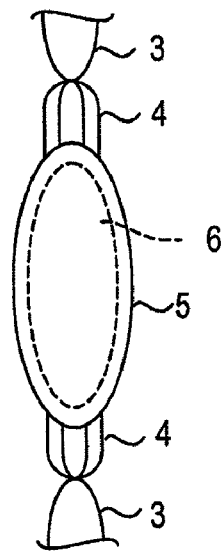
Figure 2B:
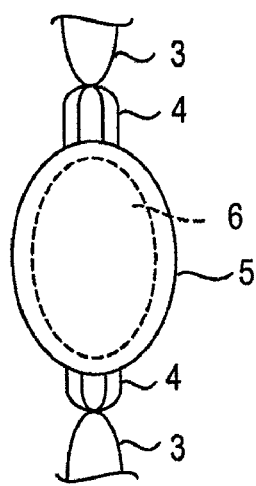

FIGS. 1, 2A and 2B illustrate the structure and operation of a human eye. Eye 100 includes cornea 1, iris 2, ciliary muscles 3, ligament fibers or zonules 4, capsule 5, lens 6 and retina 7. Natural lens 6 is composed of viscous, gelatinous transparent fibers, arranged in an "onion-like" layered structure, and is disposed in transparent elastic capsule 5. Capsule 5 is joined by zonules 4 around its circumference to ciliary muscles 3, which are in turn attached to the inner surface of eye 0. Vitreous 8 is a highly viscous, transparent fluid that fills the center of eye 100.

Isolated from the eye, the relaxed capsule and lens take on a convex shape. However, when suspended within the eye by zonules 4, capsule 5 moves between a moderately convex shape (when the ciliary muscles are relaxed) and a highly convex shape (when the ciliary muscles are contracted). As shown in FIG. 2A, when ciliary muscles 3 relax, capsule 5 and lens 6 are pulled about the circumference, thereby flattening the lens. As shown in FIG. 2B, when ciliary muscles 3 contract, capsule 5 and lens 6 relax and become thicker. This allows the lens and capsule to assume a more convex shape, thus increasing the diopter power of the lens.

Additionally, various natural mechanisms affect the design requirements of the present invention. For example, during accommodation the pupil naturally stops down (i.e., reduces in diameter) which reduces the area of the natural lens that transmits light. In addition, the eye will experience the Stiles-Crawford Effect which also reduces the effective area of the natural lens. In particular, the brightness of light rays incident on cones in the eye is dependent on the angle at which those rays are incident on the cones. In particular, light rays that strike the cones perpendicular to their surface appear brighter than those that do not. As a result, the light rays passing through the periphery of the lens are less significant for proper vision.

Figure 3:
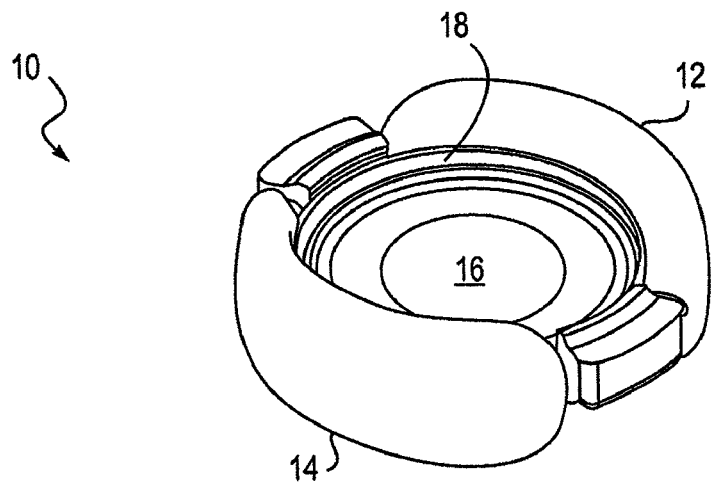
FIGS. 3-5 show an exemplary embodiment of an intraocular lens.
Figure 4:
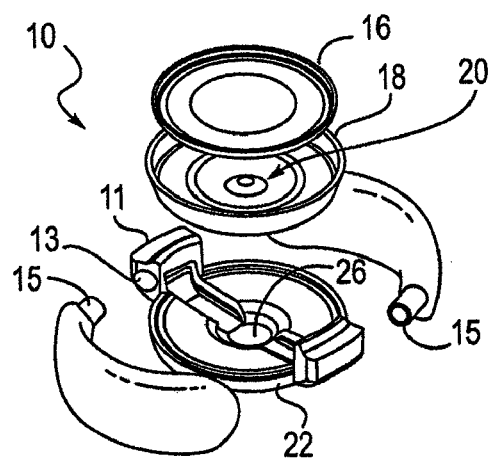
Figure 5:
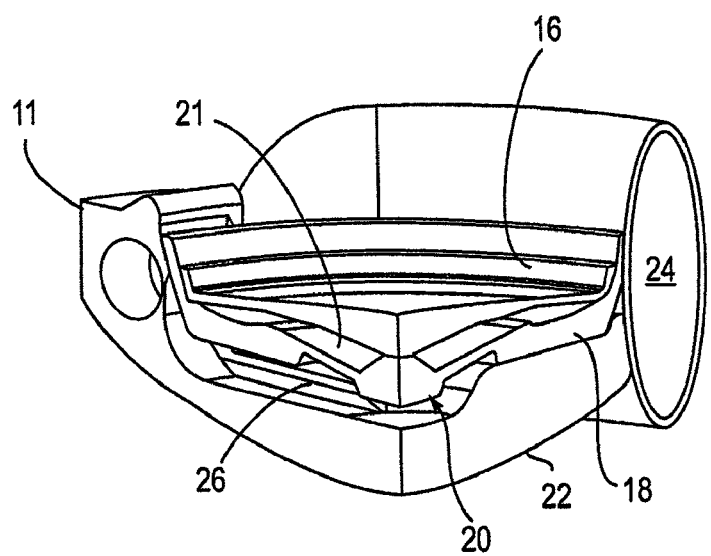

FIGS. 3-5 show a first embodiment of accommodating IOL 10 that can be tested using the system described herein. IOL 10 includes a peripheral non-optic portion comprising haptics 12 and 14. The IOL also includes an optic portion including anterior lens element 16, intermediate layer 18 which comprises actuator 20, and substrate, or posterior element, 22. Anterior element 16 is bonded to intermediate layer 18 at its periphery. In some embodiments the anterior element may also be bonded to actuator 20. The intermediate layer is also bonded to posterior element 22. The inner surface of haptics 12 and 14 define interior volumes 24 which are in fluid communication with active channel 26 defined by posterior element 22 and intermediate layer 18. As shown, actuator 20 is integral with intermediate layer 18. Posterior element 22 is molded with buttresses 11 which include a buttress bore 13 therethrough. The haptics have a haptic attachment element 15 (which can be stiff or flexible) which is sized and shaped to fit within buttress bore 13. An adhesive layer can be applied to the outer surfaces of the haptic attachment elements and/or the inner surface of the buttress bore to facilitate attachment of the haptics to the optic portion. The IOL contains a flowable media within the haptics and the active channel. The IOL also includes passive chamber 21 that is defined by the anterior element and the intermediate layer. The passive chamber contains a second flowable media (e.g., a fluid, elastomer, etc.), which may be the same as the fluid within the haptics and active channel, or it may be a different flowable media. The active channel and the passive chamber are not in fluid communication.

Deformation of haptics 12 and 14 in response to contraction of ciliary muscles movement transfers the flowable media (such as a fluid) between interior volume 24 and active channel 26. When the flowable media is transferred into the active channel from the haptics, the pressure in the active channel increases, causing actuator 20 to deflect in the anterior direction. This causes anterior element 16 to deflect in the anterior direction, increasing the IOL power in this accommodated configuration.

Figure 6:
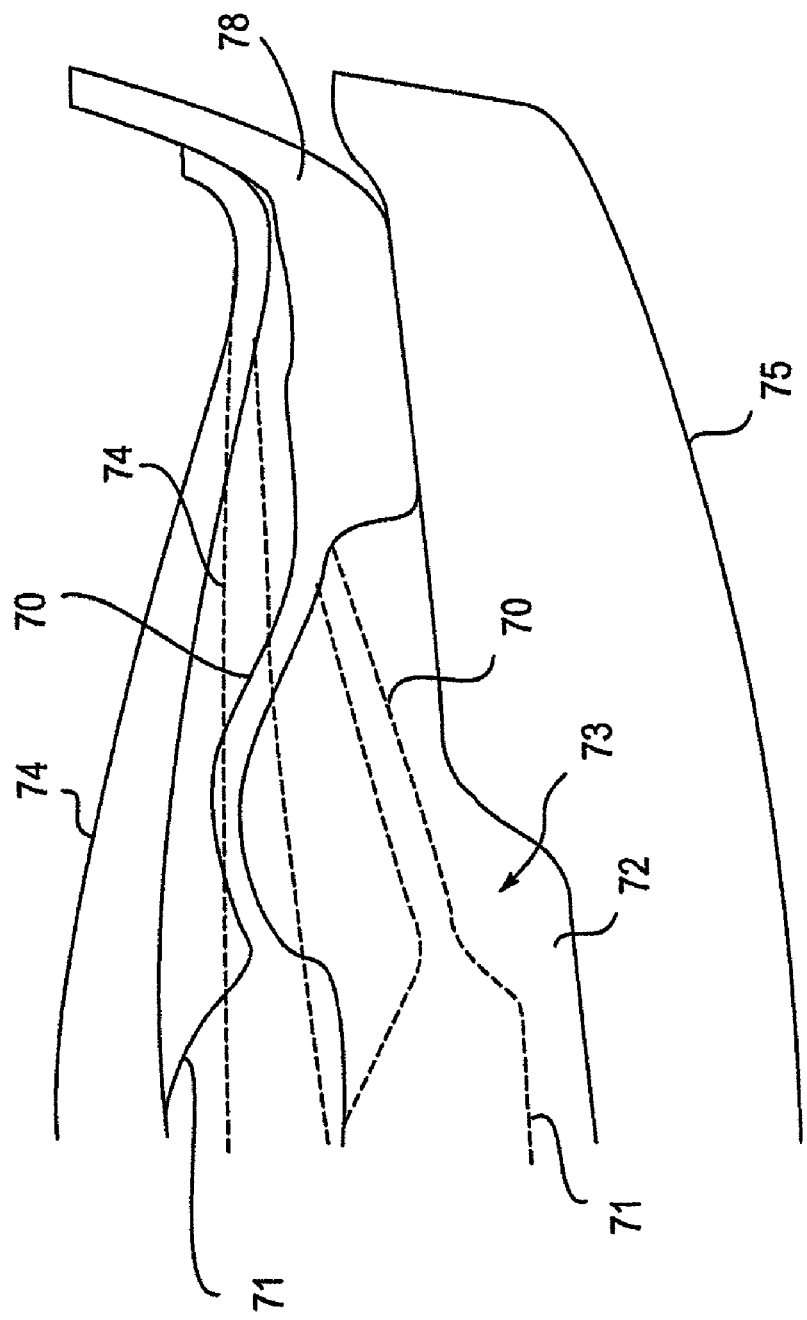
FIG. 6 shows a portion of an exemplary intraocular lens in disaccommodative and accommodative configurations.

FIG. 6 is a cross sectional view of a portion of an exemplary IOL showing the IOL in a disaccommodated state (dashed lines) and an accommodated state (solid lines). The IOL includes anterior element 74, intermediate layer 78 which includes actuator 73, and posterior element 75. Actuator 73 is comprised of deflection element 71 and bellows 70. When the pressure is increased in active channel 72, bellows 70 change configuration from the generally conical shape of the disaccommodated state to a curvilinear configuration of the accommodated state. Deflection element 71 is forced in the anterior direction due to the increase in pressure. This causes anterior element 74 to deflect in the anterior direction as well, steepening the curvature of the anterior element and thereby increasing the power of the lens.

Additional exemplary IOLs that can be tested using the systems described herein are described in U.S. Provisional Application No. 60/433,046, filed Dec. 12, 2002; U.S. Pat. Nos. 7,122,053; 7,261,737; 7,247,168; and 7,217,288; U.S. patent application Ser. No. 11/642,388, filed Dec. 19, 2006, and U.S. patent application Ser. No. 11/646,913, filed Dec. 27, 2006, the disclosures of which are hereby incorporated herein by reference.

The systems described herein can also be used to test any other suitable accommodating IOL which is adapted to change power in response to ciliary muscle movement. For example, an accommodating IOL comprised entirely of a polymeric material can be tested in the systems described herein.

The systems and devices described herein are generally used to test and analyze an IOL's accommodative response to a force applied to the lens. The accommodative response can be any detectable change in the IOL. Exemplary detectable responses include, without limitation, a change in dimension of the lens or a portion of the lens, a change in configuration of the lens or a portion of the lens, a change in shape from a first shape to a second shape, etc.

The change can be measured by almost any means, including optical, mechanical, electrical, etc. In some cases the change may also be detected by the human eye. This may not, however, be as reliable.

The systems and devices can also be used generally to test the strength of an IOL. That is, in response to a force applied to the IOL, the devices can test how well the IOL responds to those forces, and at what point the IOL begins to, for example, fatigue, fracture, etc.

The force can be applied to any portion of the IOL, but in some embodiments it is applied to a peripheral portion of the an IOL that is adapted to contact the lens capsule when implanted in the eye. The direction of the force can be applied in almost any direction, but in some embodiments the force is applied radially inward and is applied to a peripheral portion of the IOL.

Figure 7A:
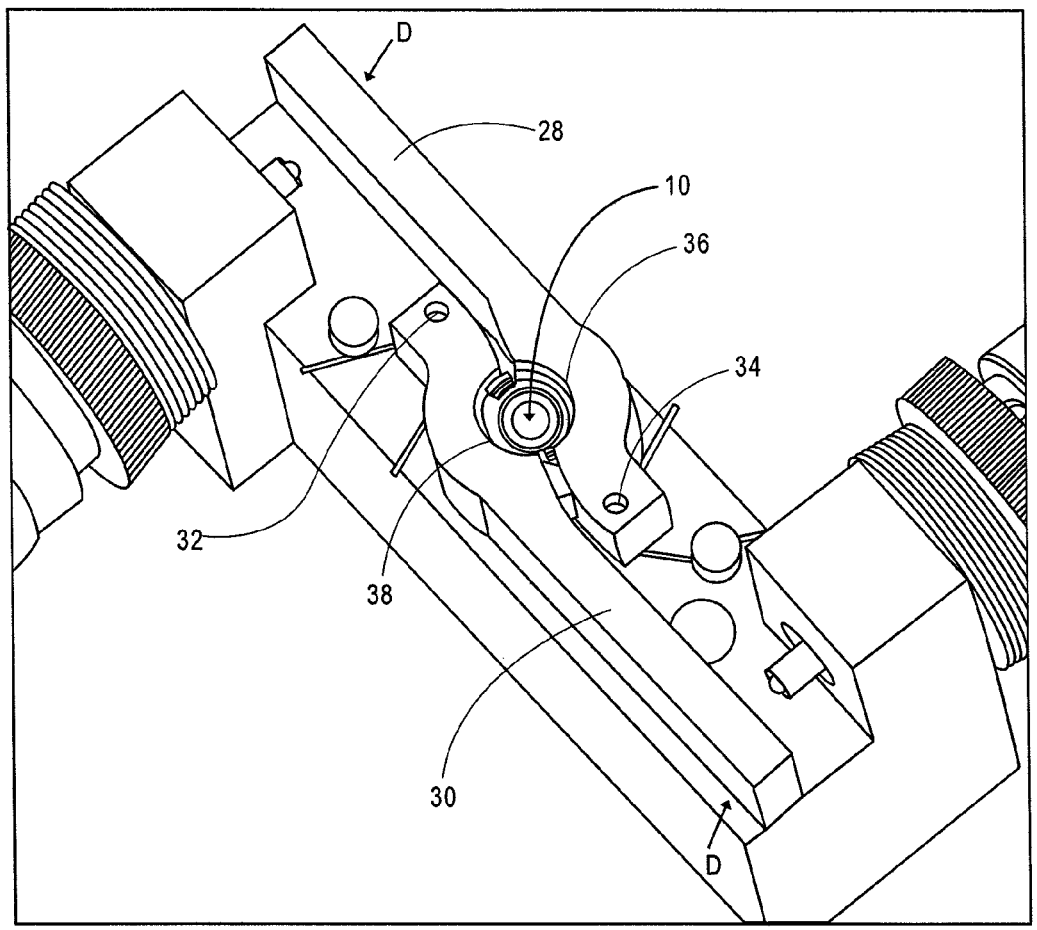
FIGS. 7A and 7B illustrate an exemplary intraocular lens testing device.
Figure 7B:
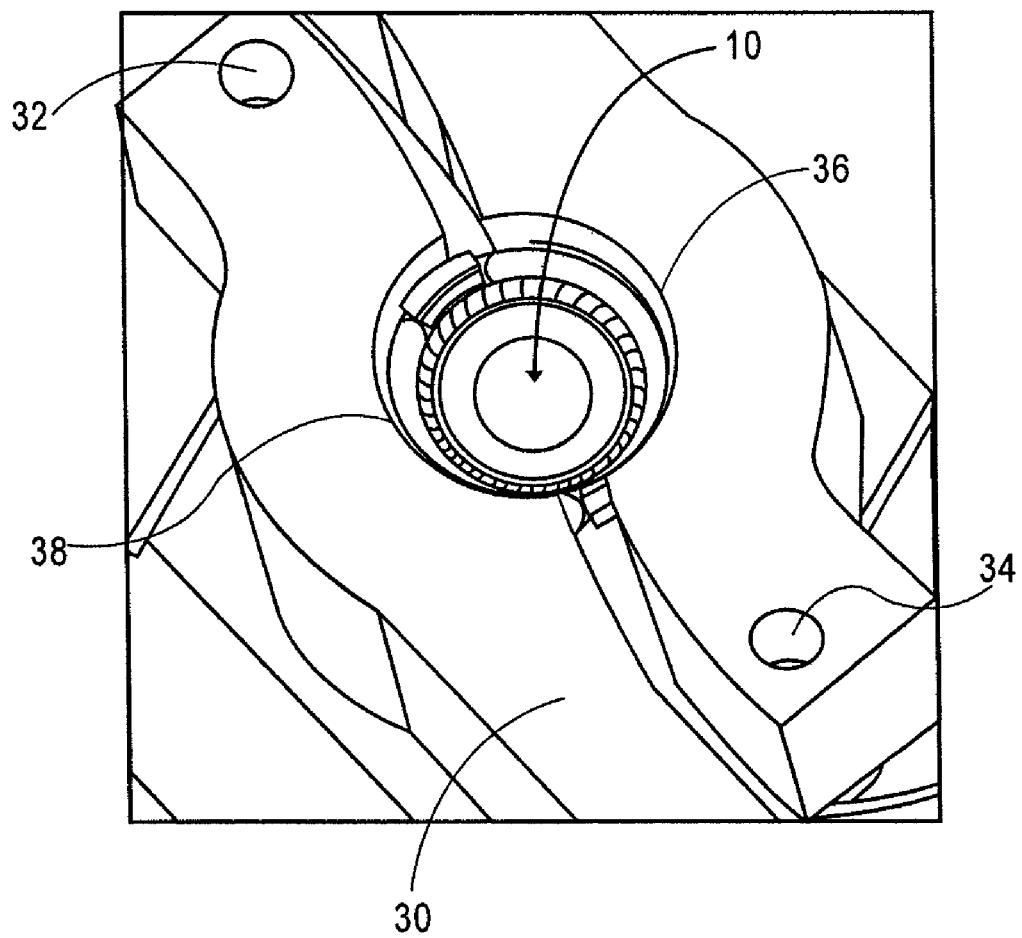

FIGS. 7A and 7B show an exemplary embodiment of a testing device used to test and analyze the radial compression and/or strength of IOL 10, which is also shown in FIGS. 3-5. The testing device includes arms 28 and 30 which pivot about pivot points 34 and 32, respectively. From the position shown in FIG. 7A, the arms are actuated in a counter-clockwise direction "D" which decreases the space between the two semi-circular portions 36 and 38 of arms 28 and 30, thus engaging haptics 12 and 14 and radially compressing the lens. The testing device can be used to measure and relate a compressive force applied to the haptics to the responsive change in the anterior element of the IOL. In reference to FIG. 6, the compressive force is measured and related to the change in the height of anterior element along a center point of the optic portion. That is, the change in height is the distance from the anterior surface of anterior element 74 in the disaccommodated state (dashed lines) to the anterior surface of anterior element 74 in the accommodated state (solid lines), along the center of the optic portion.

The change can be measured in almost way. For example, at substantially the center of the lens the thickness of the assembly can be measured from the posterior side of the posterior lens element to the anterior side of the anterior lens element. Alternatively, the thickness can be assessed by measuring the central height of the lens relative to a reference measurement such an outer edge of the optic.

As the arms are rotated, they compress the lens in a radial direction, causing a decrease in lens diameter and an increase in optic portion height. The height is increased as fluid is squeezed from the haptics and into the optic portion, causing anterior deflection of the anterior element of the lens.

Figure 8A:
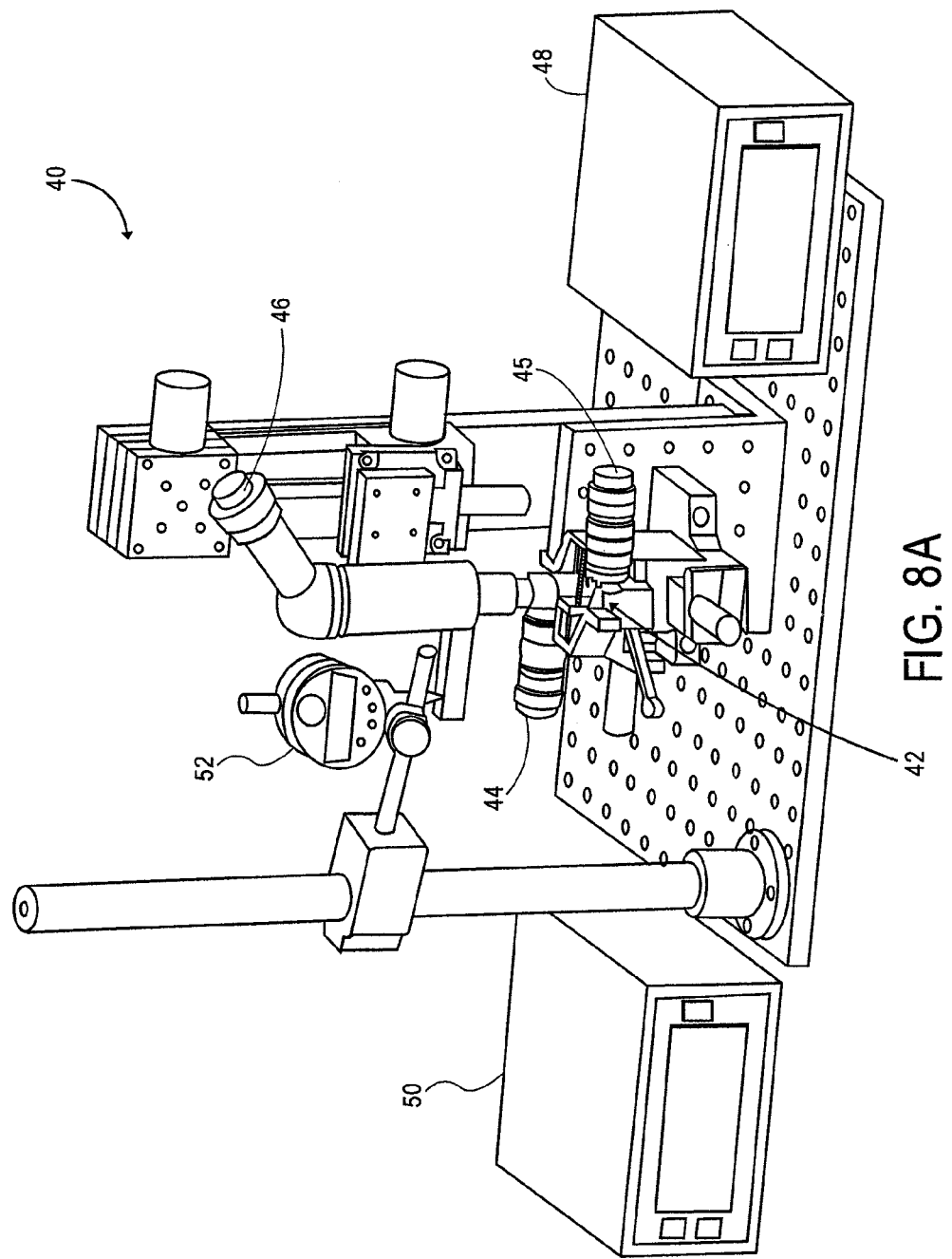
FIGS. 8A-8D show an exemplary intraocular lens testing system.
Figure 8B:
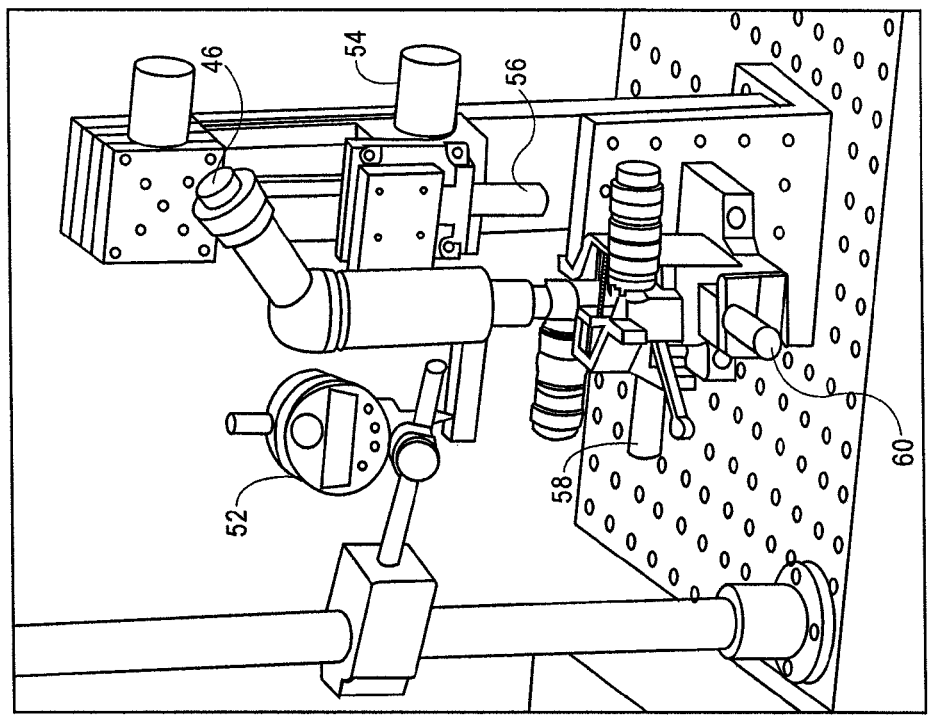
Figure 8C:
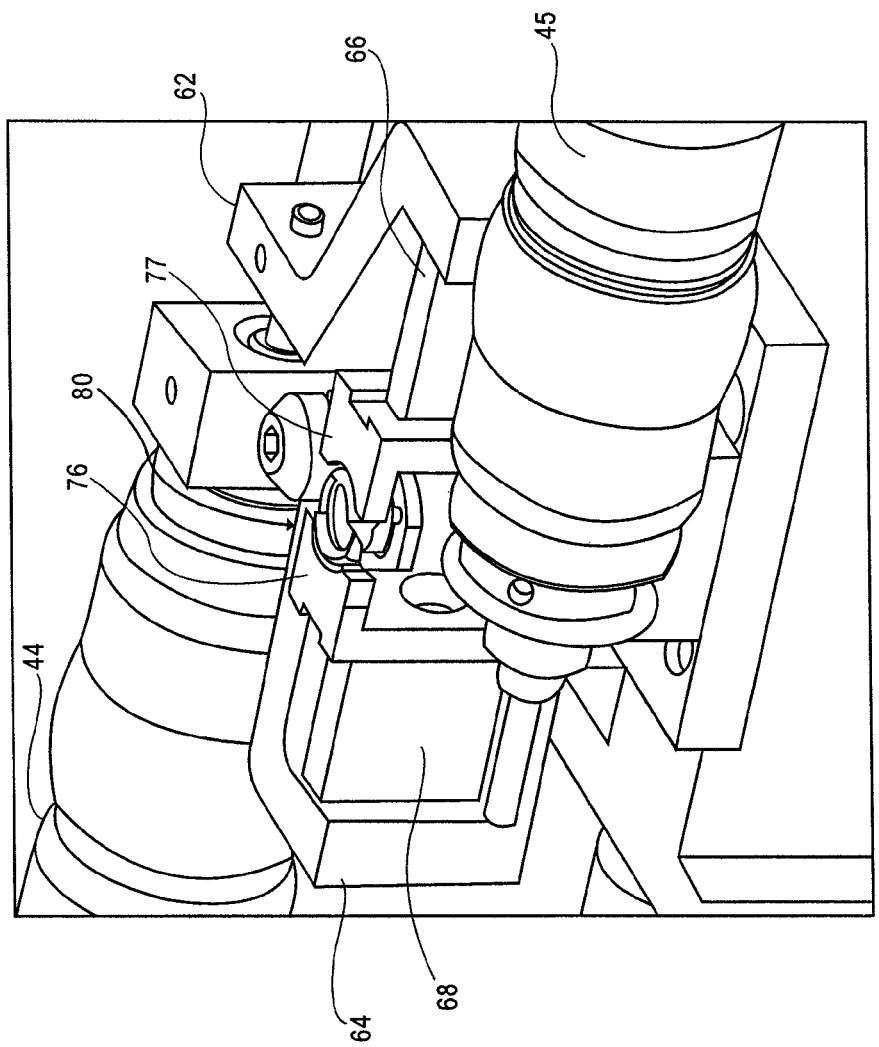
Figure 8D:
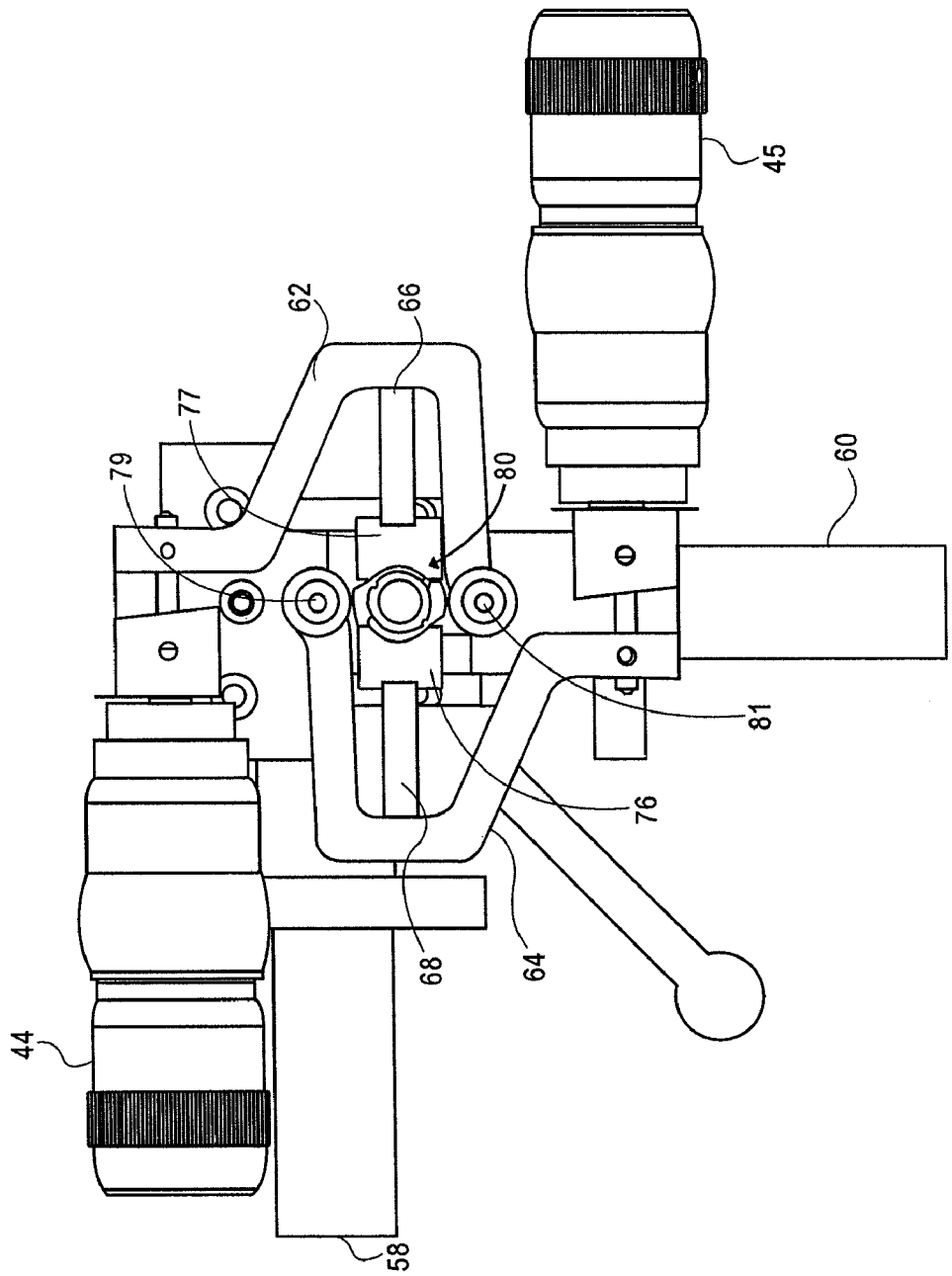

FIGS. 8A-8D illustrate an exemplary embodiment of radial compression system 40. System 40 includes IOL placement location 42 (shown in more detail in FIGS. 8C and 8D), radial compression actuators 44 and 45, microscope 46, force readouts 48 and 50, and lens surface indicator 52. As shown in FIG. 8B, the system also includes microscope course z-axis adjustor 56 and microscope fine z-axis adjustor 54. System 40 also includes X and Y positioners 58 and 60 for centering IOL 80 in IOL placement location 42. As shown in more detail in the perspective view and the top view of FIG. 8C and FIG. 8D, respectively, the system includes radial compression actuators 44 and 45 which are coupled to and adapted to actuate arms 62 and 64, respectively (In FIG. 8C, a portion of arm 64 is not shown for clarity). Arms 62 and 64 pivot around pivot 81 and 79, respectively, when actuated by radial compression actuators 44 and 45. Arms 62 and 64 are coupled to load cells 66 and 68, respectively. Load cells 66 and 68 are coupled to lens compression effectors 77 and 76, respectively. The compression effectors as shown are disposed substantially opposite each other around the periphery of the intraocular lens.

When the radial compression actuators actuate the arms, the lens compression effectors radially compress IOL 80 in the IOL placement location.

In use, IOL 80 is placed in IOL placement location 42 and X and Y positioners 58 and 60 are adjusted to center the IOL. Radial compression actuators 44 and 45 are then actuated (manually or automatically) to cause effectors 77 and 81 to radially compress IOL 80. In some embodiments the radial compression actuators are adjusted symmetrically during a test cycle. A surface of the effectors adjacent the IOL is curved to correspond to the curve of the periphery of the IOL.

The radial compression forces can be adapted to mimic forces that will be applied to the IOL (and particularly the forces applied to the periphery of the IOL) by the lens capsule in order to measure how the IOL responds to in-the-capsule conditions.

The load cells of the system can detect the amount of force (e.g., compressive force) applied to the IOL at each of the effectors. Force readouts 48 and 50 are adapted to display the amount of force applied to the IOL. The raw or analyzed data can of course by stored on any kind of computer system. As the amount of force that is applied the IOL is adjusted, a user actuates (or they are automatically actuated) the course and fine microscope z-position adjustors so microscope 46 senses the focus plane on the top (e.g., anterior) surface of the IOL. The microscope can focus on the top surface of the IOL and therefore detect the highest point on the anterior surface of the IOL for any given amount of force applied by the effectors. In this way the systems knows, for a given amount of force(s) applied to the IOL, how much the anterior element is deflecting. Lens surface indicator 52 is adapted to give a readout of the location of the lens surface. Raw or analyzed data can of course be stored in a computer system.

The testing device can be used to test alternative IOL designs or it can be used to test an IOL to make sure it is within tolerances.

Some intraocular lenses are adapted to be adjusted after being implanted in the lens capsule. Exemplary IOLs that can be adjusted post-implant are described in co-pending U.S. application Ser. No. 12/178,304, filed Jul. 23, 2008, the disclosure of which is incorporated by reference herein. For example, some IOLs can be actuated by an external energy source to alter the volume and/or pressure within the IOL, or to displace a flowable media from a first portion of the IOL to a second portion. The testing systems described herein can be adapted to test the IOL's accommodative response based on the application of energy from an external energy source.

For example, an IOL adapted to be adjusted post-implant can be placed in the IOL placement location and the effectors can be actuated (via the radial compression actuators) to cause the effectors to contact (i.e., engage) the IOL. The effectors can be further actuated to compress the peripheral haptics to mimic, for example, a capsule that has contracted, or shrunk, around the peripheral portion of the IOL after the IOL has been implanted in the capsule (which can be a natural response to an IOL implantation procedure). The microscope can be used to sense a first focus plane with the haptics in the compressed configuration. The IOL is then actuated with an external energy source (e.g., a laser) to actuate a portion of the lens to adjust the pressure and/or volume of the IOL, to displace fluid from a first portion of the lens to a second portion of the lens, or any other post-implant adjustment that may be needed to be made. The microscope is then used to sense the focus plane after the IOL has been adjusted. In this manner in can be determined how much the lens has disaccommodated or accommodated in response to the simulated post-implant adjustment.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of testing an accommodative response of an accommodating intraocular lens, comprising:
    applying a force to an accommodating intraocular lens when the accommodating intraocular lens is outside of a lens capsule; and
    measuring an accommodative response of the accommodating intraocular lens to the applied force, wherein applying a force to the accommodating intraocular lens comprises applying a compressive force to the accommodating intraocular lens.

2. The method of claim 1 wherein applying a force to the accommodating intraocular lens comprises applying a force to a peripheral portion of the accommodating intraocular lens.

3. The method of claim 1 wherein applying a compressive force comprises applying a radially compressive force to the accommodating intraocular lens.

4. The method of claim 1 wherein applying a force to the accommodating intraocular lens comprises displacing a flowable media within the accommodating intraocular lens from a peripheral portion of the accommodating intraocular lens to an optic portion of the accommodating intraocular lens.

5. The method of claim 1 wherein measuring an accommodating response of the accommodating intraocular lens comprises measuring the deflection of a surface of the accommodating intraocular lens.

6. The method of claim 1 wherein measuring the deflection of a surface of the accommodating intraocular lens comprises measuring the deflection of an anterior surface of the accommodating intraocular lens.

7. The method of claim 1 wherein measuring an accommodative response of the accommodating intraocular lens comprises optically measuring an accommodative response of the accommodating intraocular lens.

8. The method of claim 1 further comprising measuring the force applied to the accommodating intraocular lens and relating it to the measured accommodative response.

9. The method of claim 1 wherein measuring an accommodative response of the accommodating intraocular lens comprises measuring a change of configuration of the lens or a portion of the lens.

10. The method of claim 1 wherein measuring an accommodative response of the accommodating intraocular lens to the applied force comprises measuring an accommodative response of an optic portion of the accommodating intraocular lens to the applied force.

11. The method of claim 1 wherein applying a force to the accommodating intraocular lens simulates a force applied to the accommodating intraocular lens from a native capsular bag.

12. The method of claim 1 wherein measuring an accommodative response comprises measuring a change in optical power of the accommodating intraocular lens in response to the applied force.

13. A system for measuring an accommodative response of an accommodating intraocular lens outside of a lens capsule, comprising:
    a force effector adapted to apply a compressive force on an accommodating intraocular lens; and
    an accommodative response measuring element adapted to measure an accommodative response of the accommodating intraocular lens to the compressive force applied by the force effector.

14. The system of claim 13 wherein the force effector is adapted to apply a radially compressive force on the accommodating intraocular lens.

15. The system of claim 13 wherein the force effector is a first force effector and the system further comprises a second force effector, wherein the first force effector is disposed substantially opposite the second force effector around the periphery of the accommodating intraocular lens.

16. The system of claim 13 wherein the force effector is a first force effector and the system further comprises a second force effector, wherein the first force effector is adapted to be actuated with a first compression actuator to apply a force to the accommodating intraocular lens and the second force effector is adapted to be actuated with a second compression actuator to apply a second force to the accommodating intraocular lens.

17. The system of claim 13 wherein the system further comprises a force measuring element adapted to measure the force applied to the accommodating intraocular lens.

18. The system of claim 17 wherein the force measuring element is a load cell.

19. The system of claim 13 wherein the accommodative response measuring element is adapted to measure deflection of a surface of the accommodating intraocular lens.

20. The system of claim 19 wherein the accommodative response measuring element comprises a microscope adapted to sense a focus plane on a surface of the accommodating intraocular lens.

21. The system of claim 13 further comprising the accommodating intraocular lens.

* * * * *

UNITED STATES PATENT AND TRADEMARK OFFICE
CERTIFICATE OF CORRECTION

| | |
|---|---|
| PATENT NO. | : 8,314,927 B2 |
| APPLICATION NO. | : 12/178454 |
| DATED | : November 20, 2012 |
| INVENTOR(S) | : Choi et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 352 days.

Signed and Sealed this
Eighteenth Day of November, 2014

Michelle K. Lee
*Deputy Director of the United States Patent and Trademark Office*